(12) United States Patent
Boulais

(10) Patent No.: US 7,241,263 B2
(45) Date of Patent: Jul. 10, 2007

(54) SELECTIVELY ROTATABLE SHAFT COUPLER

(75) Inventor: Dennis R. Boulais, Danielson, CT (US)

(73) Assignee: Scimed Life Systems, Inc., Maple Grove, MN (US)

( * ) Notice: Subject to any disclaimer, the term of this patent is extended or adjusted under 35 U.S.C. 154(b) by 64 days.

(21) Appl. No.: 10/955,960

(22) Filed: Sep. 30, 2004

(65) Prior Publication Data

US 2006/0069307 A1   Mar. 30, 2006

(51) Int. Cl.
*A61B 1/00* (2006.01)
(52) U.S. Cl. ............ 600/137; 600/106; 600/131; 403/78; 403/164; 403/165
(58) Field of Classification Search ............ 600/106, 600/137; 403/78, 164–165
See application file for complete search history.

(56) References Cited

U.S. PATENT DOCUMENTS

| | | | |
|---|---|---|---|
| 3,266,059 A | 8/1966 | Stelle | |
| 3,470,876 A | 10/1969 | Barchilon | |
| 3,572,325 A | 3/1971 | Bazell et al. | |
| 3,581,738 A | 6/1971 | Moore | |
| 4,108,211 A | 8/1978 | Tanaka | |
| 4,286,585 A | 9/1981 | Ogawa | |
| 4,294,162 A | 10/1981 | Fowler et al. | |
| 4,315,309 A | 2/1982 | Coli | |
| 4,351,323 A | 9/1982 | Ouchi et al. | |
| 4,425,113 A | 1/1984 | Bilstad | |
| 4,432,349 A | 2/1984 | Oshiro | |
| 4,471,766 A | 9/1984 | Terayama | |
| 4,473,841 A | 9/1984 | Murakoshi et al. | |
| 4,488,039 A | 12/1984 | Sato et al. | |
| 4,491,865 A | 1/1985 | Danna et al. | |
| 4,495,134 A | 1/1985 | Ouchi et al. | |
| 4,499,895 A | 2/1985 | Takayama | |
| 4,513,235 A | 4/1985 | Acklam et al. | |
| 4,515,444 A | 5/1985 | Prescott et al. | |
| 4,516,063 A | 5/1985 | Kaye et al. | |
| 4,519,391 A | 5/1985 | Murakoshi | |
| 4,559,928 A | 12/1985 | Takayama | |
| 4,573,450 A | 3/1986 | Arakawa | |
| 4,580,210 A | 4/1986 | Nordstrom | |
| 4,586,923 A | 5/1986 | Gould et al. | |
| 4,615,330 A | 10/1986 | Nagasaki et al. | |
| 4,616,630 A | 10/1986 | Arakawa | |
| 4,617,915 A | 10/1986 | Arakawa | |
| 4,621,618 A | 11/1986 | Omagari et al. | |

(Continued)

FOREIGN PATENT DOCUMENTS

EP   0 689 851 A1   1/1996

(Continued)

*Primary Examiner*—Linda C. M. Dvorak
*Assistant Examiner*—Matthew J. Kasztejna
(74) *Attorney, Agent, or Firm*—Klarquist Sparkman, LLP

(57) ABSTRACT

In one aspect, the present invention is a system for rotatably coupling a shaft to a housing. The system includes a selectively rotatable shaft coupler that connects a shaft to a housing that allows a limited amount of shaft rotation, but which sets a restriction on the maximum amount of shaft rotation. In another aspect, the invention provides a shaft coupling system for connecting a proximal end of an endoscope shaft to a housing without the use of adhesive or epoxies.

8 Claims, 10 Drawing Sheets

U.S. PATENT DOCUMENTS

| | | |
|---|---|---|
| 4,625,714 A | 12/1986 | Toyota |
| 4,631,582 A | 12/1986 | Nagasaki et al. |
| 4,633,303 A | 12/1986 | Nagasaki et al. |
| 4,633,304 A | 12/1986 | Nagasaki |
| 4,643,170 A | 2/1987 | Miyazaki et al. |
| 4,646,723 A | 3/1987 | Arakawa |
| 4,649,904 A | 3/1987 | Krauter et al. |
| 4,651,202 A | 3/1987 | Arakawa |
| 4,652,093 A | 3/1987 | Stephen et al. |
| 4,652,916 A | 3/1987 | Suzaki et al. |
| 4,654,701 A | 3/1987 | Yabe |
| RE32,421 E | 5/1987 | Hattori |
| 4,662,360 A * | 5/1987 | O'Hara et al. .............. 600/200 |
| 4,662,725 A | 5/1987 | Nisioka |
| 4,663,657 A | 5/1987 | Nagasaki et al. |
| 4,667,655 A | 5/1987 | Ogiu et al. |
| 4,674,844 A | 6/1987 | Nishioka et al. |
| 4,686,963 A | 8/1987 | Cohen et al. |
| 4,697,210 A | 9/1987 | Toyota et al. |
| 4,700,693 A | 10/1987 | Lia et al. |
| 4,714,075 A | 12/1987 | Krauter et al. |
| 4,716,457 A | 12/1987 | Matsuo |
| 4,719,508 A | 1/1988 | Sasaki et al. |
| 4,727,417 A | 2/1988 | Kanno et al. |
| 4,727,418 A | 2/1988 | Kato et al. |
| 4,745,470 A | 5/1988 | Yabe et al. |
| 4,745,471 A | 5/1988 | Takamura et al. |
| 4,746,974 A | 5/1988 | Matsuo |
| 4,748,970 A | 6/1988 | Nakajima |
| 4,755,029 A | 7/1988 | Okabe |
| 4,762,119 A | 8/1988 | Allred et al. |
| 4,765,312 A | 8/1988 | Sasa et al. |
| 4,766,489 A | 8/1988 | Kato |
| 4,787,369 A | 11/1988 | Allred et al. |
| 4,790,294 A | 12/1988 | Allred et al. |
| 4,794,913 A | 1/1989 | Shimonaka et al. |
| 4,796,607 A | 1/1989 | Allred et al. |
| 4,800,869 A | 1/1989 | Nakajima |
| 4,805,596 A | 2/1989 | Hatori |
| 4,806,011 A | 2/1989 | Bettinger |
| 4,819,065 A | 4/1989 | Eino |
| 4,819,077 A | 4/1989 | Kikuchi et al. |
| 4,821,116 A | 4/1989 | Nagasaki et al. |
| 4,824,225 A | 4/1989 | Nishioka |
| 4,831,437 A | 5/1989 | Nishioka et al. |
| 4,836,187 A | 6/1989 | Iwakoshi et al. |
| 4,844,052 A | 7/1989 | Iwakoshi et al. |
| 4,844,071 A | 7/1989 | Chen et al. |
| 4,845,553 A | 7/1989 | Konomura et al. |
| 4,845,555 A | 7/1989 | Yabe et al. |
| 4,847,694 A | 7/1989 | Nishihara |
| 4,853,772 A | 8/1989 | Kikuchi |
| 4,860,731 A | 8/1989 | Matsuura |
| 4,867,546 A | 9/1989 | Nishioka et al. |
| 4,868,647 A | 9/1989 | Uehara et al. |
| 4,869,237 A | 9/1989 | Eino et al. |
| 4,873,965 A | 10/1989 | Danieli |
| 4,875,468 A | 10/1989 | Krauter et al. |
| 4,877,314 A | 10/1989 | Kanamori |
| 4,882,623 A | 11/1989 | Uchikubo |
| 4,884,134 A | 11/1989 | Tsuji et al. |
| 4,885,634 A | 12/1989 | Yabe |
| 4,890,159 A | 12/1989 | Ogiu |
| 4,894,715 A | 1/1990 | Uchikubo et al. |
| 4,895,431 A | 1/1990 | Tsujiuchi et al. |
| 4,899,731 A | 2/1990 | Takayama et al. |
| 4,899,732 A | 2/1990 | Cohen |
| 4,899,787 A | 2/1990 | Ouchi et al. |
| 4,905,666 A | 3/1990 | Fukuda |
| 4,918,521 A | 4/1990 | Yabe et al. |
| 4,919,112 A | 4/1990 | Siegmund |
| 4,919,114 A | 4/1990 | Miyazaki |
| 4,920,980 A | 5/1990 | Jackowski |
| 4,928,172 A | 5/1990 | Uehara et al. |
| 4,931,867 A | 6/1990 | Kikuchi |
| 4,941,454 A | 7/1990 | Wood et al. |
| 4,941,456 A | 7/1990 | Wood et al. |
| 4,951,134 A | 8/1990 | Nakasima et al. |
| 4,951,135 A | 8/1990 | Sasagawa et al. |
| 4,952,040 A | 8/1990 | Igarashi |
| 4,960,127 A | 10/1990 | Noce et al. |
| 4,961,110 A | 10/1990 | Nakamura |
| 4,967,269 A | 10/1990 | Sasagawa et al. |
| 4,971,034 A | 11/1990 | Doi et al. |
| 4,973,311 A | 11/1990 | Iwakoshi et al. |
| 4,979,497 A | 12/1990 | Matsuura et al. |
| 4,982,725 A | 1/1991 | Hibino et al. |
| 4,984,878 A | 1/1991 | Miyano |
| 4,986,642 A | 1/1991 | Yokota et al. |
| 4,987,884 A | 1/1991 | Nishioka et al. |
| 4,989,075 A | 1/1991 | Ito |
| 4,989,581 A | 2/1991 | Tamburrino et al. |
| 4,996,974 A | 3/1991 | Ciarlei |
| 4,996,975 A | 3/1991 | Nakamura |
| 4,998,182 A | 3/1991 | Krauter et al. |
| 5,001,556 A | 3/1991 | Nakamura et al. |
| 5,005,558 A | 4/1991 | Aomori |
| 5,005,957 A | 4/1991 | Kanamori et al. |
| 5,007,408 A | 4/1991 | Ieoka |
| 5,018,509 A | 5/1991 | Suzuki et al. |
| 5,022,382 A | 6/1991 | Ohshoi et al. |
| 5,029,016 A | 7/1991 | Hiyama et al. |
| 5,034,888 A | 7/1991 | Uehara et al. |
| 5,040,069 A | 8/1991 | Matsumoto et al. |
| RE33,689 E | 9/1991 | Nishioka et al. |
| 5,045,935 A | 9/1991 | Kikuchi |
| 5,049,989 A | 9/1991 | Tsuji |
| 5,050,584 A | 9/1991 | Matsuura |
| 5,050,974 A | 9/1991 | Takasugi et al. |
| 5,056,503 A | 10/1991 | Nagasaki |
| 5,061,994 A | 10/1991 | Takahashi |
| 5,068,719 A | 11/1991 | Tsuji |
| 5,081,524 A | 1/1992 | Tsuruoka et al. |
| 5,087,989 A | 2/1992 | Igarashi |
| 5,110,645 A | 5/1992 | Matsumoto et al. |
| 5,111,281 A | 5/1992 | Sekiguchi |
| 5,111,306 A | 5/1992 | Kanno et al. |
| 5,111,804 A | 5/1992 | Funakoshi |
| 5,113,254 A | 5/1992 | Kanno et al. |
| 5,119,238 A | 6/1992 | Igarashi |
| 5,131,393 A | 7/1992 | Ishiguro et al. |
| 5,137,013 A | 8/1992 | Chiba et al. |
| 5,140,265 A | 8/1992 | Sakiyama et al. |
| 5,159,446 A | 10/1992 | Hibino et al. |
| 5,170,775 A | 12/1992 | Tagami |
| 5,172,225 A | 12/1992 | Takahashi et al. |
| 5,174,293 A | 12/1992 | Hagiwara |
| 5,176,629 A | 1/1993 | Kullas et al. |
| 5,188,093 A * | 2/1993 | Lafferty et al. ............. 600/109 |
| 5,191,878 A | 3/1993 | Iida et al. |
| 5,198,931 A | 3/1993 | Igarashi |
| 5,201,908 A | 4/1993 | Jones |
| 5,208,702 A | 5/1993 | Shiraiwa |
| 5,209,220 A | 5/1993 | Hiyama et al. |
| 5,225,958 A | 7/1993 | Nakamura |
| 5,228,356 A | 7/1993 | Chuang |
| 5,243,416 A | 9/1993 | Nakazawa |
| 5,243,967 A | 9/1993 | Hibino |
| 5,257,628 A | 11/1993 | Ishiguro et al. |
| 5,271,381 A | 12/1993 | Ailinger et al. |
| RE34,504 E | 1/1994 | Uehara et al. |
| 5,291,010 A | 3/1994 | Tsuji |
| 5,299,559 A | 4/1994 | Bruce et al. |
| 5,311,858 A | 5/1994 | Adair |

| | | | | | |
|---|---|---|---|---|---|
| 5,325,845 A | 7/1994 | Adair et al. | 5,812,983 A | 9/1998 | Kumagai |
| 5,331,551 A | 7/1994 | Tsuruoka et al. | 5,819,736 A | 10/1998 | Avny et al. |
| 5,342,299 A | 8/1994 | Snoke et al. | 5,820,591 A | 10/1998 | Thompson et al. |
| 5,347,989 A | 9/1994 | Monroe et al. | 5,821,466 A | 10/1998 | Clark et al. |
| 5,374,953 A | 12/1994 | Sasaki et al. | 5,821,920 A | 10/1998 | Rosenberg et al. |
| 5,379,757 A | 1/1995 | Hiyama et al. | 5,823,948 A | 10/1998 | Ross, Jr. et al. |
| 5,381,782 A | 1/1995 | DeLaRama et al. | 5,827,186 A | 10/1998 | Chen et al. |
| 5,383,791 A | 1/1995 | Hirakui et al. | 5,827,190 A | 10/1998 | Palcic et al. |
| 5,390,662 A | 2/1995 | Okada | 5,828,197 A | 10/1998 | Martin et al. |
| 5,400,769 A | 3/1995 | Tanii et al. | 5,828,363 A | 10/1998 | Yaniger et al. |
| 5,402,768 A | 4/1995 | Adair | 5,830,124 A | 11/1998 | Suzuki et al. |
| 5,402,769 A | 4/1995 | Tsuji | 5,830,128 A | 11/1998 | Tanaka |
| 5,409,485 A | 4/1995 | Suda | 5,836,869 A | 11/1998 | Kudo et al. |
| 5,412,478 A | 5/1995 | Ishihara et al. | 5,837,023 A | 11/1998 | Koike et al. |
| 5,418,649 A | 5/1995 | Igarashi | 5,840,014 A | 11/1998 | Miyano et al. |
| 5,420,644 A | 5/1995 | Watanabe | 5,841,126 A | 11/1998 | Fossum et al. |
| 5,431,645 A | 7/1995 | Smith et al. | 5,843,000 A | 12/1998 | Nishioka et al. |
| 5,434,615 A | 7/1995 | Matumoto | 5,846,183 A | 12/1998 | Chilcoat |
| 5,436,640 A | 7/1995 | Reeves | 5,855,560 A | 1/1999 | Idaomi et al. |
| 5,436,767 A | 7/1995 | Suzuki et al. | 5,857,963 A | 1/1999 | Pelchy et al. |
| 5,440,341 A | 8/1995 | Suzuki et al. | 5,865,724 A | 2/1999 | Palmer et al. |
| 5,464,007 A | 11/1995 | Krauter et al. | 5,868,664 A | 2/1999 | Speier et al. |
| 5,469,840 A | 11/1995 | Tanii et al. | 5,868,666 A | 2/1999 | Okada et al. |
| 5,473,235 A | 12/1995 | Lance et al. | 5,873,816 A | 2/1999 | Kagawa et al. |
| 5,482,029 A | 1/1996 | Sekiguchi et al. | 5,873,866 A | 2/1999 | Kondo et al. |
| 5,484,407 A | 1/1996 | Osypka | 5,876,326 A | 3/1999 | Takamura et al. |
| 5,485,316 A | 1/1996 | Mori et al. | 5,876,331 A | 3/1999 | Wu et al. |
| 5,496,260 A | 3/1996 | Krauter et al. | 5,876,373 A | 3/1999 | Giba et al. |
| 5,515,449 A | 5/1996 | Tsuruoka et al. | 5,876,427 A | 3/1999 | Chen et al. |
| 5,518,501 A | 5/1996 | Oneda et al. | 5,877,819 A | 3/1999 | Branson |
| 5,543,831 A | 8/1996 | Tsuji et al. | 5,879,284 A | 3/1999 | Tsujita |
| 5,569,158 A | 10/1996 | Suzuki et al. | 5,880,714 A | 3/1999 | Rosenberg et al. |
| 5,569,159 A | 10/1996 | Anderson et al. | 5,882,293 A | 3/1999 | Ouchi |
| 5,586,262 A | 12/1996 | Komatsu et al. | 5,882,339 A | 3/1999 | Beiser et al. |
| 5,589,854 A | 12/1996 | Tsai | 5,889,670 A | 3/1999 | Schuler et al. |
| 5,591,202 A | 1/1997 | Slater et al. | 5,889,672 A | 3/1999 | Schuler et al. |
| 5,608,451 A | 3/1997 | Konno et al. | 5,892,630 A | 4/1999 | Broome |
| 5,619,380 A | 4/1997 | Agasawa et al. | 5,895,350 A | 4/1999 | Hori |
| 5,622,528 A | 4/1997 | Hamano et al. | 5,897,507 A | 4/1999 | Kortenbach et al. |
| 5,631,695 A | 5/1997 | Nakamura et al. | 5,897,525 A | 4/1999 | Dey et al. |
| 5,633,203 A | 5/1997 | Adair | 5,907,487 A | 5/1999 | Rosenberg et al. |
| 5,643,203 A | 7/1997 | Beiser et al. | 5,923,018 A | 7/1999 | Kameda et al. |
| 5,645,075 A | 7/1997 | Palmer et al. | 5,928,136 A | 7/1999 | Barry |
| 5,647,840 A | 7/1997 | D'Amelio et al. | 5,929,607 A | 7/1999 | Rosenberg et al. |
| 5,658,238 A | 8/1997 | Suzuki et al. | 5,929,846 A | 7/1999 | Rosenberg et al. |
| 5,667,477 A | 9/1997 | Segawa | 5,929,900 A | 7/1999 | Yamanaka et al. |
| 5,674,182 A | 10/1997 | Suzuki et al. | 5,929,901 A | 7/1999 | Adair et al. |
| 5,674,197 A | 10/1997 | van Muiden et al. | 5,931,833 A | 8/1999 | Silverstein |
| 5,685,823 A | 11/1997 | Ito et al. | 5,933,809 A | 8/1999 | Hunt et al. |
| 5,685,825 A | 11/1997 | Takase et al. | 5,935,085 A | 8/1999 | Welsh et al. |
| 5,691,853 A | 11/1997 | Miyano | 5,936,778 A | 8/1999 | Miyano et al. |
| 5,695,450 A | 12/1997 | Yabe et al. | 5,941,817 A | 8/1999 | Crawford |
| 5,698,866 A | 12/1997 | Doiron et al. | 5,950,168 A | 9/1999 | Simborg et al. |
| 5,702,349 A | 12/1997 | Morizumi | 5,951,462 A | 9/1999 | Yamanaka |
| 5,703,724 A | 12/1997 | Miyano | 5,956,416 A | 9/1999 | Tsuruoka et al. |
| 5,704,371 A | 1/1998 | Shepard | 5,956,689 A | 9/1999 | Everhart |
| 5,704,896 A | 1/1998 | Fukunishi et al. | 5,956,690 A | 9/1999 | Haggerson et al. |
| 5,708,482 A | 1/1998 | Takahashi et al. | 5,959,613 A | 9/1999 | Rosenberg et al. |
| 5,721,566 A | 2/1998 | Rosenberg et al. | 5,976,070 A | 11/1999 | Ono et al. |
| 5,724,068 A | 3/1998 | Sanchez et al. | 5,976,074 A | 11/1999 | Moriyama |
| 5,728,045 A | 3/1998 | Komi | 5,980,454 A | 11/1999 | Broome |
| 5,739,811 A | 4/1998 | Rosenberg et al. | 5,980,468 A | 11/1999 | Zimmon |
| 5,740,801 A | 4/1998 | Branson | 5,986,693 A | 11/1999 | Adair et al. |
| 5,746,696 A | 5/1998 | Kondo | 5,991,729 A | 11/1999 | Barry et al. |
| 5,764,809 A | 6/1998 | Nomami et al. | 5,991,730 A | 11/1999 | Lubin et al. |
| 5,767,839 A | 6/1998 | Rosenberg | 5,999,168 A | 12/1999 | Rosenberg et al. |
| 5,781,172 A | 7/1998 | Engel et al. | 6,002,425 A | 12/1999 | Yamanaka et al. |
| 5,782,752 A * | 7/1998 | Lichtman et al. ........... 600/137 | 6,007,531 A | 12/1999 | Snoke et al. |
| 5,788,714 A | 8/1998 | Ouchi | 6,014,630 A | 1/2000 | Jeacock et al. |
| 5,789,047 A | 8/1998 | Sasaki et al. | 6,015,088 A | 1/2000 | Parker et al. |
| 5,793,539 A | 8/1998 | Konno et al. | 6,017,322 A | 1/2000 | Snoke et al. |
| 5,805,140 A | 9/1998 | Rosenberg et al. | 6,020,875 A | 2/2000 | Moore et al. |
| 5,810,715 A | 9/1998 | Moriyama | 6,020,876 A | 2/2000 | Rosenberg et al. |

| | | | | |
|---|---|---|---|---|
| 6,026,363 A | 2/2000 | Shepard | 6,449,006 B1 | 9/2002 | Shipp |
| 6,030,360 A | 2/2000 | Biggs | 6,453,190 B1 | 9/2002 | Acker et al. |
| 6,032,120 A | 2/2000 | Rock et al. | 6,454,162 B1 | 9/2002 | Teller |
| 6,039,728 A | 3/2000 | Berlien et al. | 6,459,447 B1 | 10/2002 | Okada et al. |
| 6,043,839 A | 3/2000 | Adair et al. | 6,460,319 B2 * | 10/2002 | Marshall et al. ............... 56/233 |
| 6,050,718 A | 4/2000 | Schena et al. | 6,468,204 B2 | 10/2002 | Sendai et al. |
| 6,057,828 A | 5/2000 | Rosenberg et al. | 6,475,141 B2 | 11/2002 | Abe |
| 6,059,719 A | 5/2000 | Yamamoto et al. | 6,478,730 B1 | 11/2002 | Bala et al. |
| 6,061,004 A | 5/2000 | Rosenberg | 6,489,987 B1 | 12/2002 | Higuchi et al. |
| 6,063,035 A | 5/2000 | Sakamoto | 6,496,827 B2 | 12/2002 | Kozam et al. |
| 6,067,077 A | 5/2000 | Martin et al. | 6,498,948 B1 | 12/2002 | Ozawa et al. |
| 6,071,248 A | 6/2000 | Zimmon | 6,503,193 B1 | 1/2003 | Iwasaki et al. |
| 6,075,555 A | 6/2000 | Street | 6,520,908 B1 | 2/2003 | Ikeda et al. |
| 6,078,308 A | 6/2000 | Rosenberg et al. | 6,524,234 B2 | 2/2003 | Ouchi |
| 6,078,353 A | 6/2000 | Yamanaka et al. | 6,530,882 B1 | 3/2003 | Farkas et al. |
| 6,078,876 A | 6/2000 | Rosenberg et al. | 6,533,722 B2 | 3/2003 | Nakashima |
| 6,080,104 A | 6/2000 | Ozawa et al. | 6,540,669 B2 | 4/2003 | Abe et al. |
| 6,081,809 A | 6/2000 | Kumagai | 6,544,194 B1 | 4/2003 | Kortenbach et al. |
| 6,083,152 A | 7/2000 | Strong | 6,545,703 B1 | 4/2003 | Takahashi et al. |
| 6,083,170 A | 7/2000 | Ben-Haim | 6,551,239 B2 | 4/2003 | Renner et al. |
| 6,095,971 A | 8/2000 | Takahashi | 6,558,317 B2 | 5/2003 | Takahashi et al. |
| 6,099,465 A | 8/2000 | Inoue | 6,561,971 B1 | 5/2003 | Akiba |
| 6,100,874 A | 8/2000 | Schena et al. | 6,565,507 B2 | 5/2003 | Kamata et al. |
| 6,104,382 A | 8/2000 | Martin et al. | 6,574,629 B1 | 6/2003 | Cooke, Jr. et al. |
| 6,120,435 A | 9/2000 | Eino | 6,589,162 B2 | 7/2003 | Nakashima et al. |
| 6,125,337 A | 9/2000 | Rosenberg et al. | 6,595,913 B2 | 7/2003 | Takahashi |
| 6,128,006 A | 10/2000 | Rosenberg et al. | 6,597,390 B1 | 7/2003 | Higuchi |
| 6,132,369 A | 10/2000 | Takahashi | 6,599,239 B2 | 7/2003 | Hayakawa et al. |
| 6,134,056 A | 10/2000 | Nakamura | 6,602,186 B1 | 8/2003 | Sugimoto et al. |
| 6,134,506 A | 10/2000 | Rosenberg et al. | 6,605,035 B2 | 8/2003 | Ando et al. |
| 6,135,946 A | 10/2000 | Konen et al. | 6,609,135 B1 | 8/2003 | Omori et al. |
| 6,139,508 A | 10/2000 | Simpson et al. | 6,611,846 B1 | 8/2003 | Stoodley |
| 6,141,037 A | 10/2000 | Upton et al. | 6,614,969 B2 | 9/2003 | Eichelberger et al. |
| 6,142,956 A | 11/2000 | Kortenbach et al. | 6,616,601 B2 | 9/2003 | Hayakawa |
| 6,146,355 A | 11/2000 | Biggs | 6,623,424 B2 | 9/2003 | Hayakawa et al. |
| 6,149,607 A | 11/2000 | Simpson et al. | 6,638,214 B2 | 10/2003 | Akiba |
| 6,152,877 A | 11/2000 | Masters | 6,638,215 B2 | 10/2003 | Kobayashi |
| 6,154,198 A | 11/2000 | Rosenberg | 6,641,528 B2 | 11/2003 | Torii |
| 6,154,248 A | 11/2000 | Ozawa et al. | 6,651,669 B1 | 11/2003 | Burnside |
| 6,155,988 A | 12/2000 | Peters | 6,656,110 B1 | 12/2003 | Irion et al. |
| 6,181,481 B1 | 1/2001 | Yamamoto et al. | 6,656,112 B2 | 12/2003 | Miyanaga |
| 6,184,922 B1 | 2/2001 | Saito et al. | 6,659,940 B2 | 12/2003 | Adler |
| 6,193,714 B1 | 2/2001 | McGaffigan et al. | 6,663,561 B2 | 12/2003 | Sugimoto et al. |
| 6,195,592 B1 | 2/2001 | Schuler et al. | 6,669,629 B2 | 12/2003 | Matsui |
| 6,203,493 B1 | 3/2001 | Ben-Haim | 6,673,012 B2 | 1/2004 | Fujii et al. |
| 6,206,824 B1 | 3/2001 | Ohara et al. | 6,677,984 B2 | 1/2004 | Kobayashi et al. |
| 6,211,904 B1 | 4/2001 | Adair | 6,678,397 B1 | 1/2004 | Ohmori et al. |
| 6,216,104 B1 | 4/2001 | Moshfeghi et al. | 6,682,479 B1 | 1/2004 | Takahashi et al. |
| 6,219,091 B1 | 4/2001 | Yamanaka et al. | 6,685,631 B2 | 2/2004 | Minami |
| 6,221,070 B1 | 4/2001 | Tu et al. | 6,686,949 B2 | 2/2004 | Kobayashi et al. |
| 6,241,668 B1 | 6/2001 | Herzog | 6,690,409 B1 | 2/2004 | Takahashi |
| 6,260,994 B1 | 7/2001 | Matsumoto et al. | 6,690,963 B2 | 2/2004 | Ben-Haim et al. |
| 6,272,470 B1 | 8/2001 | Teshima | 6,692,431 B2 * | 2/2004 | Kazakevich ................ 600/178 |
| 6,275,255 B1 | 8/2001 | Adair et al. | 6,697,101 B1 | 2/2004 | Takahashi et al. |
| 6,283,960 B1 | 9/2001 | Ashley | 6,699,181 B2 | 3/2004 | Wako |
| 6,295,082 B1 | 9/2001 | Dowdy et al. | 6,702,737 B2 | 3/2004 | Hino et al. |
| 6,299,625 B1 | 10/2001 | Bacher | 6,711,426 B2 | 3/2004 | Benaron et al. |
| 6,309,347 B1 | 10/2001 | Takahashi et al. | 6,715,068 B1 | 3/2004 | Abe |
| 6,310,642 B1 | 10/2001 | Adair et al. | 6,716,162 B2 | 4/2004 | Hakamata |
| 6,319,196 B1 | 11/2001 | Minami | 6,728,599 B2 | 4/2004 | Wang et al. |
| 6,319,197 B1 | 11/2001 | Tsuji et al. | 6,730,018 B2 | 5/2004 | Takase |
| 6,334,844 B1 | 1/2002 | Akiba | 6,736,773 B2 | 5/2004 | Wendlandt et al. |
| 6,346,075 B1 | 2/2002 | Arai et al. | 6,743,240 B2 | 6/2004 | Smith et al. |
| 6,366,799 B1 | 4/2002 | Acker et al. | 6,749,559 B1 | 6/2004 | Kraas et al. |
| 6,381,029 B1 | 4/2002 | Tipirneni | 6,749,560 B1 | 6/2004 | Konstorum et al. |
| 6,398,724 B1 | 6/2002 | May et al. | 6,749,561 B2 | 6/2004 | Kazakevich |
| 6,413,207 B1 | 7/2002 | Minami | 6,753,905 B1 | 6/2004 | Okada et al. |
| 6,421,078 B1 | 7/2002 | Akai et al. | 6,758,806 B2 | 7/2004 | Kamrava et al. |
| 6,425,535 B1 | 7/2002 | Akiba | 6,758,807 B2 | 7/2004 | Minami |
| 6,425,858 B1 | 7/2002 | Minami | 6,758,842 B2 | 7/2004 | Irion et al. |
| 6,436,032 B1 | 8/2002 | Eto et al. | 6,778,208 B2 | 8/2004 | Takeshige et al. |
| 6,441,845 B1 | 8/2002 | Matsumoto | 6,780,151 B2 | 8/2004 | Grabover et al. |
| 6,447,444 B1 | 9/2002 | Avni et al. | 6,785,410 B2 | 8/2004 | Vining et al. |

| | | |
|---|---|---|
| 6,785,593 B2 | 8/2004 | Wang et al. |
| 6,796,938 B2 | 9/2004 | Sendai |
| 6,796,939 B1 | 9/2004 | Hirata et al. |
| 6,798,533 B2 | 9/2004 | Tipirneni |
| 6,800,056 B2 | 10/2004 | Tartaglia et al. |
| 6,800,057 B2 | 10/2004 | Tsujita et al. |
| 6,808,491 B2 | 10/2004 | Kortenbach et al. |
| 6,817,976 B2 * | 11/2004 | Rovegno .............. 600/173 |
| 6,824,539 B2 | 11/2004 | Novak |
| 6,824,548 B2 | 11/2004 | Smith et al. |
| 6,829,003 B2 | 12/2004 | Takami |
| 6,830,545 B2 | 12/2004 | Bendall |
| 6,832,990 B2 | 12/2004 | Kortenbach et al. |
| 6,840,932 B2 | 1/2005 | Lang et al. |
| 6,842,196 B1 | 1/2005 | Swift et al. |
| 6,846,286 B2 | 1/2005 | Suzuki et al. |
| 6,847,933 B1 | 1/2005 | Hastings |
| 6,849,043 B2 | 2/2005 | Kondo |
| 6,850,794 B2 | 2/2005 | Shahidi |
| 6,855,109 B2 | 2/2005 | Obata et al. |
| 6,858,004 B1 | 2/2005 | Ozawa et al. |
| 6,858,014 B2 | 2/2005 | Damarati |
| 6,860,849 B2 | 3/2005 | Matsushita et al. |
| 6,863,650 B1 | 3/2005 | Irion |
| 6,863,661 B2 | 3/2005 | Carrillo et al. |
| 6,868,195 B2 | 3/2005 | Fujita |
| 6,871,086 B2 | 3/2005 | Nevo et al. |
| 6,873,352 B2 | 3/2005 | Mochida et al. |
| 6,876,380 B2 | 4/2005 | Abe et al. |
| 6,879,339 B2 | 4/2005 | Ozawa |
| 6,881,188 B2 | 4/2005 | Furuya et al. |
| 6,882,785 B2 | 4/2005 | Eichelberger et al. |
| 6,887,195 B1 | 5/2005 | Pilvisto |
| 6,890,294 B2 | 5/2005 | Niwa et al. |
| 6,892,090 B2 | 5/2005 | Verard et al. |
| 6,892,112 B2 | 5/2005 | Wang et al. |
| 6,895,268 B1 | 5/2005 | Rahn et al. |
| 6,898,086 B2 | 5/2005 | Takami et al. |
| 6,899,673 B2 | 5/2005 | Ogura et al. |
| 6,899,674 B2 | 5/2005 | Viebach et al. |
| 6,899,705 B2 | 5/2005 | Niemeyer |
| 6,900,829 B1 | 5/2005 | Ozawa et al. |
| 6,902,527 B1 | 6/2005 | Doguchi et al. |
| 6,902,529 B2 | 6/2005 | Onishi et al. |
| 6,903,761 B1 | 6/2005 | Abe et al. |
| 6,903,883 B2 | 6/2005 | Amanai |
| 6,905,057 B2 | 6/2005 | Swayze et al. |
| 6,905,462 B1 | 6/2005 | Homma |
| 6,908,427 B2 | 6/2005 | Fleener et al. |
| 6,908,429 B2 | 6/2005 | Heimberger et al. |
| 6,911,916 B1 | 6/2005 | Wang et al. |
| 6,916,286 B2 | 7/2005 | Kazakevich |
| 6,923,818 B2 | 8/2005 | Muramatsu et al. |
| 6,928,490 B1 | 8/2005 | Bucholz et al. |
| 6,930,706 B2 | 8/2005 | Kobayahi et al. |
| 6,932,761 B2 | 8/2005 | Maeda et al. |
| 6,934,093 B2 | 8/2005 | Kislev et al. |
| 6,934,575 B2 | 8/2005 | Ferre et al. |
| 6,943,663 B2 | 9/2005 | Wang et al. |
| 6,943,946 B2 | 9/2005 | Fiete |
| 6,943,959 B2 | 9/2005 | Homma |
| 6,943,966 B2 | 9/2005 | Konno |
| 6,944,031 B2 | 9/2005 | Takami et al. |
| 6,949,068 B2 | 9/2005 | Taniguchi et al. |
| 6,950,691 B2 | 9/2005 | Uchikubo |
| 6,955,671 B2 | 10/2005 | Uchikubo |
| 2001/0039370 A1 | 11/2001 | Takahashi et al. |
| 2001/0049491 A1 | 12/2001 | Shimada |
| 2002/0017515 A1 | 2/2002 | Obata et al. |
| 2002/0028984 A1 | 3/2002 | Hayakawa et al. |
| 2002/0055669 A1 | 5/2002 | Konno |
| 2002/0080248 A1 | 6/2002 | Adair et al. |
| 2002/0087048 A1 | 7/2002 | Brock et al. |
| 2002/0087166 A1 | 7/2002 | Brock et al. |
| 2002/0095175 A1 | 7/2002 | Brock et al. |
| 2002/0128633 A1 | 9/2002 | Brock et al. |
| 2002/0193664 A1 | 12/2002 | Ross et al. |
| 2003/0034863 A1 | 2/2003 | Kazakevich |
| 2003/0069897 A1 | 4/2003 | Roy et al. |
| 2003/0149338 A1 | 8/2003 | Francois et al. |
| 2003/0181905 A1 | 9/2003 | Long |
| 2004/0049097 A1 | 3/2004 | Miyake |
| 2004/0054258 A1 | 3/2004 | Maeda et al. |
| 2004/0073083 A1 | 4/2004 | Ikeda et al. |
| 2004/0073084 A1 | 4/2004 | Meada et al. |
| 2004/0073085 A1 | 4/2004 | Ikeda et al. |
| 2004/0147809 A1 | 7/2004 | Kazakevich |
| 2004/0167379 A1 | 8/2004 | Akiba |
| 2004/0249247 A1 | 12/2004 | Iddan |
| 2004/0257608 A1 | 12/2004 | Tipirneni |
| 2005/0197861 A1 | 9/2005 | Omori et al. |
| 2005/0203341 A1 | 9/2005 | Welker et al. |
| 2005/0228697 A1 | 10/2005 | Funahashi |
| 2005/0273084 A1 | 12/2005 | Hinman et al. |

FOREIGN PATENT DOCUMENTS

| | | |
|---|---|---|
| EP | 1 300 883 A2 | 4/2003 |
| JP | 58-78635 A | 5/1983 |
| JP | 05-31071 A | 2/1993 |
| JP | 05-091972 A | 4/1993 |
| JP | 06-105800 | 4/1994 |
| JP | 06-254048 A | 9/1994 |
| JP | 07-8441 A | 1/1995 |
| JP | 10-113330 A | 5/1998 |
| JP | 10-286221 A | 10/1998 |
| JP | 11-216113 A | 8/1999 |
| JP | 3219521 B2 | 8/2001 |
| JP | 2002-102152 A | 4/2002 |
| JP | 2002-177197 A | 6/2002 |
| JP | 2002-185873 A | 6/2002 |
| JP | 2002-253481 A | 9/2002 |
| JP | 3372273 B2 | 11/2002 |
| JP | 2003-75113 A | 3/2003 |
| JP | 3482238 B2 | 10/2003 |
| WO | WO 93/13704 A1 | 7/1993 |
| WO | WO 2004/016310 A2 | 2/2004 |
| WO | WO 2005/023082 A2 | 3/2005 |

* cited by examiner

SELECTIVELY ROTATABLE SHAFT COUPLER

FIELD OF THE INVENTION

The present invention relates to shaft couplers for medical devices in general and to rotatable shaft couplers in particular.

BACKGROUND OF THE INVENTION

It has become well established that there are major health benefits from regular endoscopic examinations of a patient's internal structures such as the alimentary canals and airways, e.g., the esophagus, stomach, lungs, colon, uterus, urethra, kidney, and other organ systems. Endoscopes are also commonly used to perform surgical, therapeutic, diagnostic or other medical procedures under direct visualization. A conventional imaging endoscope used for such procedures generally include an illuminating mechanism such as a fiber optic light guide connected to a proximal source of light, and an imaging means such as an imaging light guide to carry an image to a remote camera or eye piece or a miniature video camera within the endoscope itself. In addition, most endoscopes include one or more working channels through which medical devices such as biopsy forceps, snares, fulguration probes and other tools may be passed in order to perform a procedure at a desired location in the patient's body.

In connection with the endoscope, an operator control module is typically provided that allows a user to control and steer the operation of the endoscope. The endoscope is guided through the patient's tract or canal until an opening at the distal end of the endoscope is proximate to the area of the patient's body which is to be examined or receive treatment. At this point, the endoscope allows other components, such as a catheter, to access the targeted area.

In many endoscope procedures, the physician or operator needs to rotate an endoscope shaft in order to obtain the desired images, to obtain a desired position of the distal tip, or to perform a desired surgical function (e.g. polyp removal, drainage, and the like). An endoscope shaft with low torque transfer characteristic allows for shaft rotation by allowing the shaft to twist around its central axis; however, excessive rotation of the shaft can damage the cables, tubes and electrical wires within the shaft. On the other hand, an endoscope shaft that is not allowed to rotate at all may loop over itself during clinical use, causing damage to the internal components as well as discomfort to the patient.

SUMMARY OF THE INVENTION

To address these and other problems, in one aspect the present invention is a system for rotatably coupling a shaft to a housing. The system includes a selectively rotatable shaft coupler that connects a shaft to a housing that allows a limited amount of shaft rotation, but which sets a restriction on the maximum amount of shaft rotation. The rotatable shaft coupler comprises a shaft adapter having a rotatably securable hollow body with a first end adapted to be secured to an end of a shaft and a second end adapted to be rotatably attached to a collar. A collar extends from a housing that rotatably receives the shaft adapter. At least one stop element is provided that is capable of limiting the rotation of the shaft adapter with respect to the housing.

In another aspect, the present invention provides a selectively rotatable shaft coupler that attaches an endoscope shaft to a housing and maintains the effective length of the endoscope shaft during rotation. The rotatable shaft coupler comprises a shaft adapter having a hollow body with a first end adapted to be secured to an end of a shaft, a second end adapted to be slidably connected to a rotary adapter, and a circular flange adjacent to the first end. A collar extends from the housing with a first end adapted to receive the flange on the shaft adapter and a threaded lumen with a first stop element and a second stop element, wherein the first stop element and the second stop element are spaced apart from one another at a predetermined width inside the collar. A rotary adapter is provided with a hollow body having a first end adapted to slidably connect to the second end of the shaft adapter and a second end comprising an engagement element. The engagement element rides inside the threads of the collar, and rotation of the rotary adapter in the threaded collar causes incremental movement of the rotary adapter along the collar lumen until either the engagement element contacts the first stop element on the collar, limiting further rotation in the clockwise direction, or until the engagement element contacts the second stop element on the collar, limiting further rotation in the counterclockwise direction.

In another aspect, the present invention provides a shaft coupling system for connecting a proximal end of an endoscope shaft to a housing or other structure without the use of adhesive or epoxies. The shaft coupling system comprises a housing with a first end adapted to receive a shaft retainer and a shaft retainer comprising a plurality of retention barbs capable of securing an end of an endoscope shaft.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

To address the problems associated with excessive endoscope shaft rotation, the present invention is a system for rotatably coupling a shaft to a housing. The system comprises a selectively rotatable shaft coupler that allows a limited amount of device (e.g., endoscope) shaft rotation, but which sets a restriction on the maximum amount of shaft rotation in order to provide increased manipulation of the endoscope while protecting the internal components of the shaft. Although the present invention is described as allowing rotation of an endoscope, it will be appreciated that the invention is useful with catheters, sheaths or other devices that are inserted into a patient, wherein selective rotation of a shaft with respect to another part of the device is desired.

The shaft coupler system of the present invention comprises at least one selectively rotatable shaft adapter that connects the endoscope shaft to a connector that is secured to the device to which the shaft is to be rotatably connected. In one embodiment, the shaft coupler system comprises one selectively rotatable shaft coupler positioned either proximal an endoscope connector or at a breakout box as described in U.S. patent application Ser. No. 10/811,781, filed Mar. 29, 2004, and a continuation-in-part patent application entitled VIDEO ENDOSCOPE, filed Sep. 30, 2004, and are herein incorporated by reference. In another embodiment, the shaft coupler system comprises a first rotatable shaft coupler positioned at one end of the shaft and a second rotatable shaft coupler positioned at the other end of the shaft to provide an increased rotational range.

Figure 1:
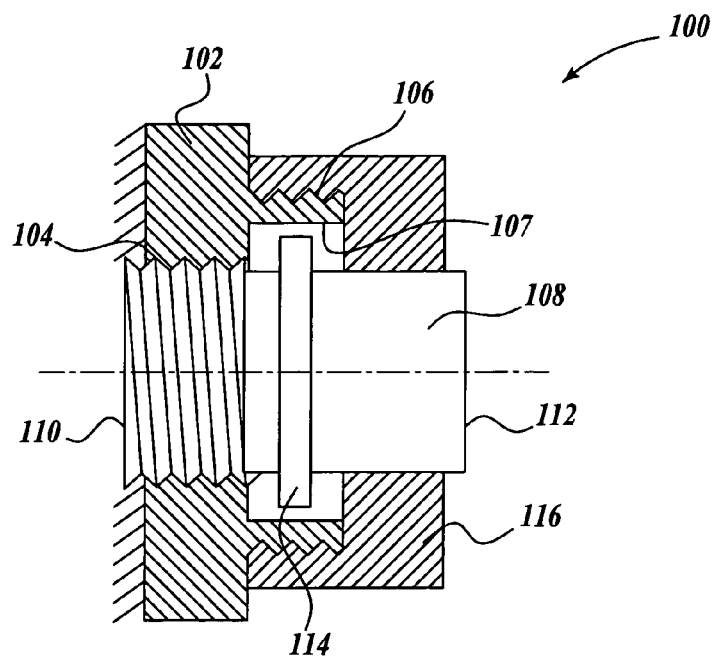
FIG. 1 is a diagram illustrating a selectively rotatable shaft coupler in accordance with one embodiment of the invention.

FIG. 1 illustrates an exemplary embodiment of a selectively rotatable shaft coupler 100 for connecting an endoscope shaft (not shown) to a proximal connector housing 102. In the embodiment shown, the proximal connector housing 102 is rigidly secured to a retainer wall of another object to which the endoscope is to be rotatably secured. The proximal connector housing has a threaded bore 104 into which a corresponding threaded end 110 of a shaft adapter 108 is inserted. The proximal connector also includes an outwardly extended threaded nipple 106 having a smooth bore 107 therein. The proximal connector housing 102 may be secured to the retainer wall by a variety of means such as an adhesive, or with any suitable fastener, or may be integrally formed with the retainer wall. The depth of the bore 107 determines the maximum range of endoscope shaft rotation.

A shaft adapter 108 has a distal threaded end 110 that is threaded within the connector housing 102 and a proximal end that is secured to an end of the endoscope. Between the distal and proximal ends of the shaft adapter is a circular flange 114. A cap 116 is threaded onto the nipple 106 to close the flange 114 in the bore 107. The shaft coupler 100 comprising the shaft adapter 108 and the connector housing 102 may be packaged as a preformed unit that is removably attached to a housing or to any desired object with any suitable connection means.

Figure 2:
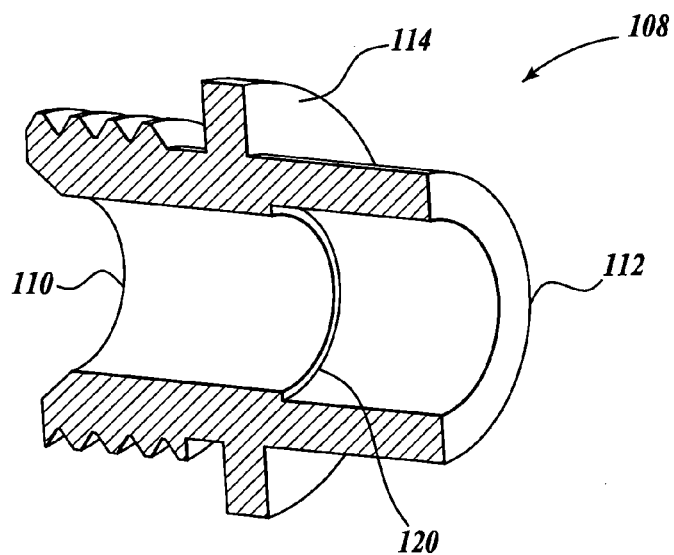
FIG. 2 shows a cross-sectional view of a shaft adapter that is included in the shaft coupler shown in FIG. 1.

FIG. 2 shows a cross-sectional view of the shaft adapter 108. As shown, the shaft adapter 108 has a hollow body with a first end 110 adapted to be threaded with the proximal connector 102 and a second end 112 adapted to be secured to the end of an endoscope. As shown, the shaft adapter body has a central hollow lumen through which control cables and other elements of the endoscope are passed to allow electrical, irrigation and aspiration connections to extend into the endoscope. A counter-bored detail 120 inside the second end 112 of the shaft adapter 108 receives an end of an endoscope shaft. Alternatively, the second end of the shaft adapter may be sized to fit inside an end of an endoscope shaft and secure the shaft by any suitable means, such as with the use of an adhesive and/or any suitable fastener.

Figure 3A:
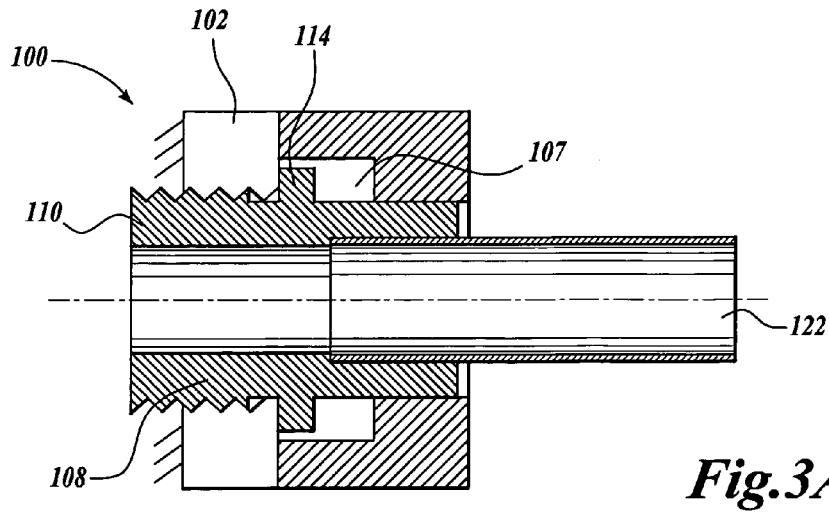
FIG. 3A is a diagram illustrating the selectively rotatable shaft adapter of FIG. 2 shown in a position of maximum rotation in a first direction.
Figure 3B:
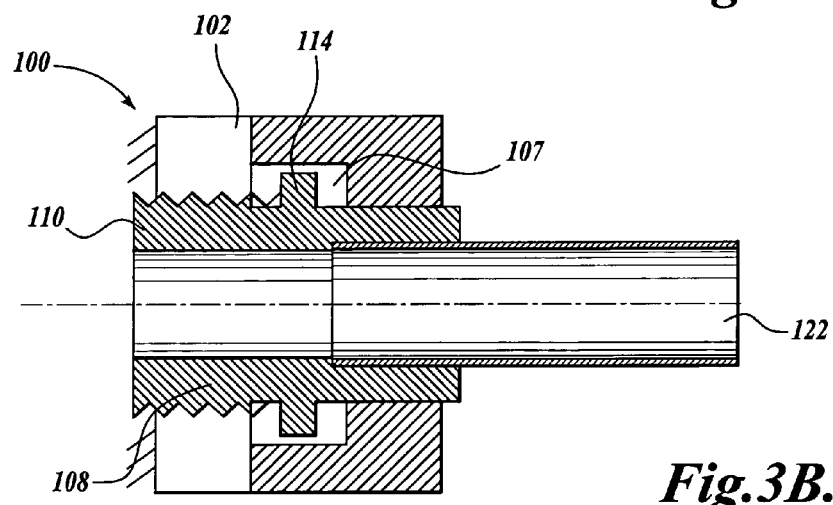
FIG. 3B shows the selectively rotatable shaft adapter of FIG. 2 shown in a position of minimal endoscope shaft rotation.
Figure 3C:
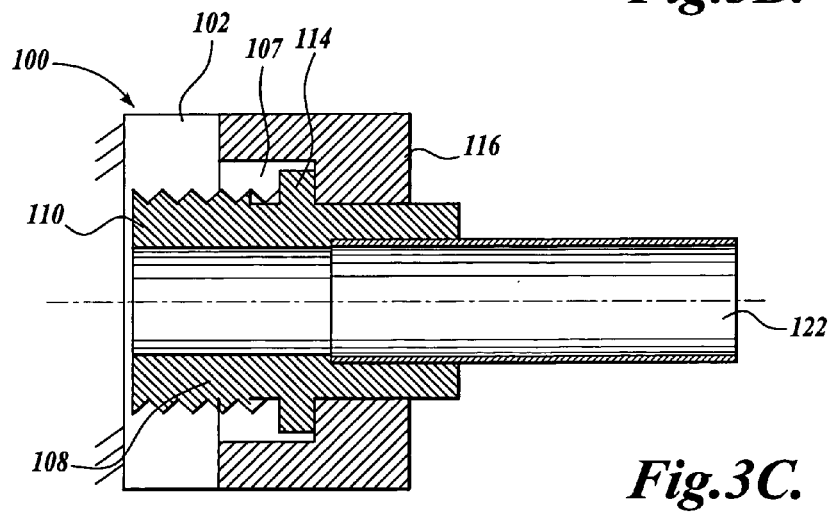
FIG. 3C shows the selectively rotatable shaft adapter of FIG. 2 coupled to an endoscope shaft showing maximum rotation in a second direction.

FIGS. 3A–C illustrate the rotational movement of the shaft adapter 108 in the proximal connector housing 102 when coupled to a rotating endoscope shaft 122. In operation, as shown in FIG. 3A, an end of an endoscope shaft 122 is first secured to the proximal end of the shaft adapter, causing the shaft adapter 108 to rotate along with the endoscope shaft 122. Rotation of the shaft 122 in a first direction (e.g. clockwise) causes axial movement of the shaft adapter 108 until the flange 114 is moved towards the bottom of the bore 107 by the threads on the distal end 110 of the shaft adapter 108. As shown in FIG. 3B, the flange 114 is in an intermediate position in the cylindrical bore 107, indicating a midway rotation of the endoscope shaft 122. Finally, as shown in FIG. 3C, rotation in a full counterclockwise direction causes axial movement of the shaft adapter 108 towards the cap 116 until the flange 114 in the bore 107 contacts the interior surface of the cap 116. The depth of the bore 107 and the width of the flange 114 and/or the pitch of the threads that secure the shaft adapter 108 to the proximal connector housing 102, may be adjusted to allow for various amounts of rotational motion of the shaft.

Figure 4:
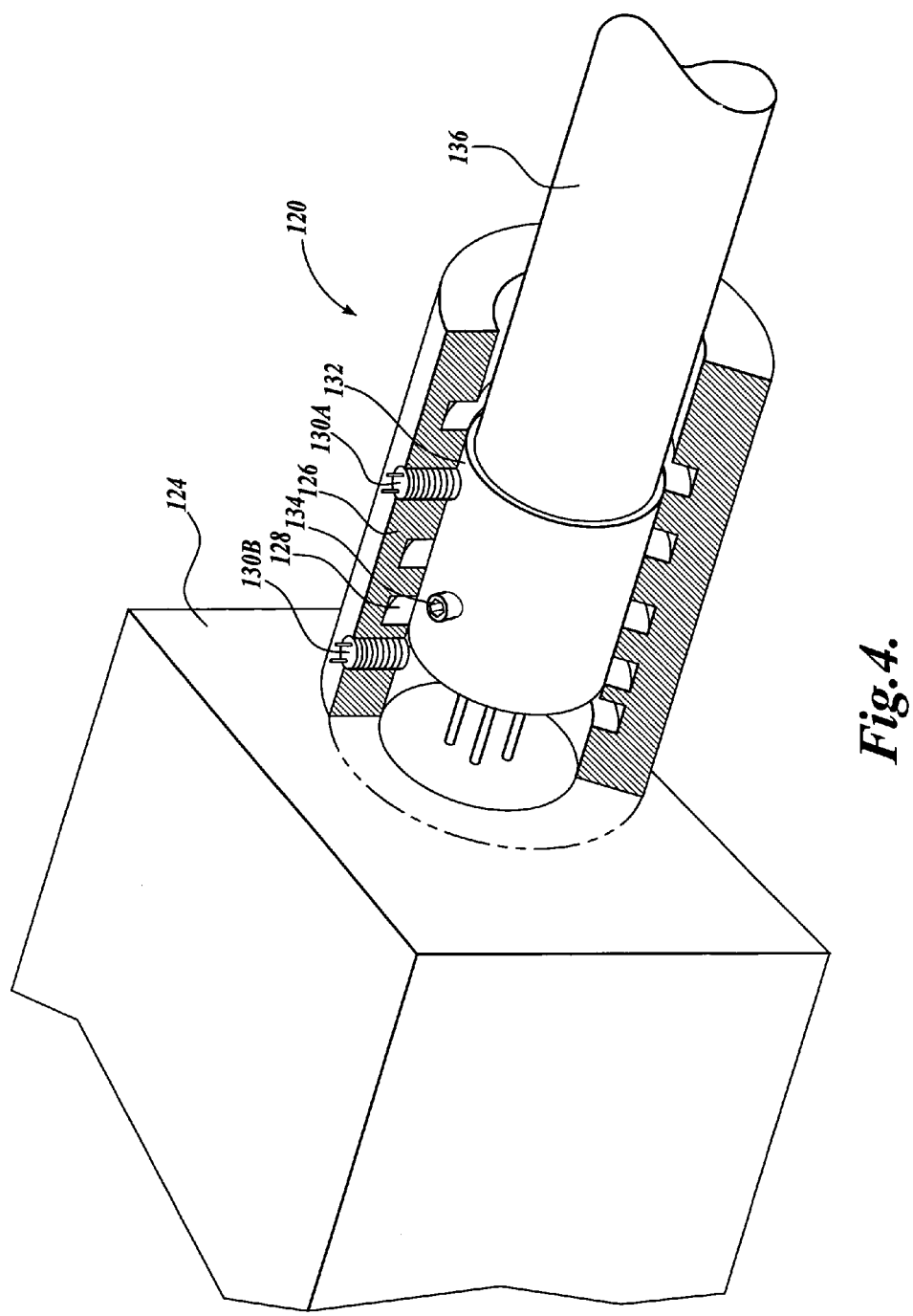
FIG. 4 illustrates another embodiment of a selectively rotatable shaft coupler in accordance with the present invention.

FIG. 4 is a partial cutaway view of another embodiment of a selectively rotatable shaft coupler 120 attached to, for example, a proximal connector housing 124. As shown, an internally threaded collar 126 extends from, or is attached to the proximal connector housing 124. A shaft adapter 132 is secured to an end of an endoscope shaft 136 and an engagement element such as a pin 134 is sized to be received in the grooves 128 of the threaded collar 126. In operation, the engagement pin 134, or other equivalent engagement element on the shaft adapter 132 rides in the grooves 128 of the threaded collar 126, causing the shaft adapter 132 to move axially in and out of the collar during rotation of the endoscope shaft 136. To limit rotation of the shaft, at least two stop elements 130A,B are positioned to extend into the threads 128 of the threaded collar to prevent movement of the engagement pin 134. The location of each of the two stop pins 130A,B in the threads determines the range of endoscope shaft rotation.

In some embodiments, the stop elements 130A,B may be tightened onto the shaft adapter 132, thereby locking the endoscope shaft 136 into a desired orientation during clinical use. Although the embodiment shown uses two stop pins 130A,B, it will be appreciated that a single stop pin could be used by limiting the depth of the threads in the collar 126.

Similarly, although the embodiment shown in FIG. 4 is described with reference to stop elements as pins, those of skill in the art will understand that the stop elements may comprise any suitable structure capable of preventing the rotation of the shaft adapter 132 in the collar 126, such as blocks, tabs and the like. Similarly, those of skill in the art will understand that a suitable engagement element is not limited to a pin, but also includes any structure capable of allowing rotation in the collar 126 such as tabs, blocks, a smaller threaded section, and the like.

Figure 5:
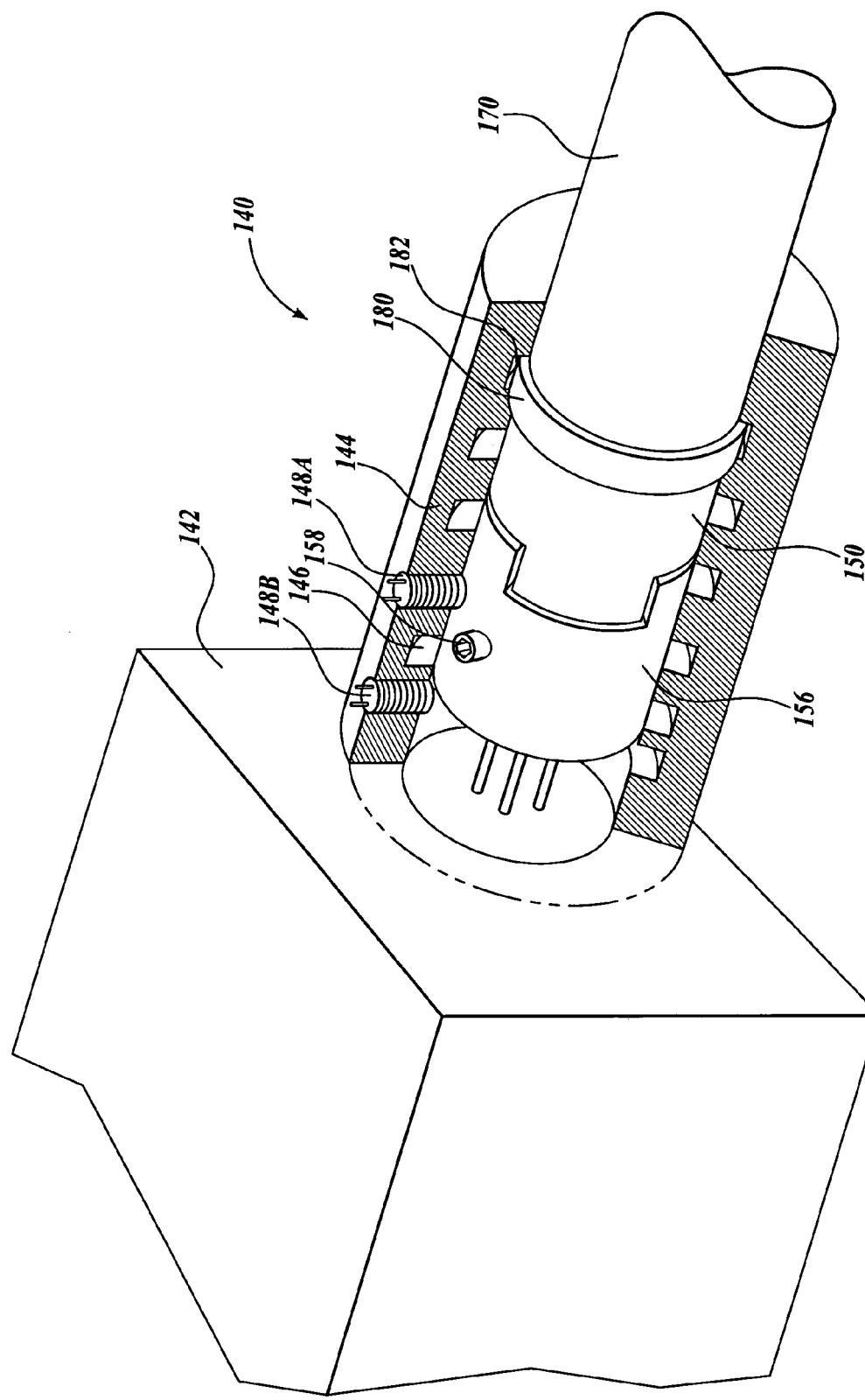
FIG. 5 illustrates another embodiment of a selectively rotatable shaft coupler that maintains the effective length of an endoscope shaft during rotation, in accordance with another embodiment of the present invention.

In another aspect, the present invention provides a selectively rotatable shaft coupler that attaches an endoscope shaft to a housing and maintains the effective length of the endoscope shaft during rotation. FIG. 5 is a partial cutaway view of another embodiment of a selectively rotatable shaft coupler 140 that extends from, or is attached to, for example, a proximal connector housing 142 in accordance with this aspect of the invention. As shown, an internally threaded collar 144 extends from and is integrally formed with, or is attached to the housing 142. An endoscope shaft 170 is secured to a first end of a shaft adapter 150. A second end of the shaft adapter 150 has alternating tangs and notches that slidably engage a corresponding set of tangs and notches on a rotary adapter 156. A circular flange 180 on the shaft adapter 150 is rotatably fitted in an annular slot 182 that extends around the interior of the collar 144.

An engagement pin 158 on the rotary adapter 156 rides in the threaded grooves 146 of the collar 144 and causes the rotary adapter 156 to move axially in and out of the collar 144 during rotation of the endoscope shaft 170. To limit rotation of the shaft, stop elements 148A,B extend into the grooves 146 of the threaded collar 144, to prevent further rotation of the engagement pin 158. The location of each of the two stop pins 148A,B determines the range of endoscope shaft rotation.

Figure 6:
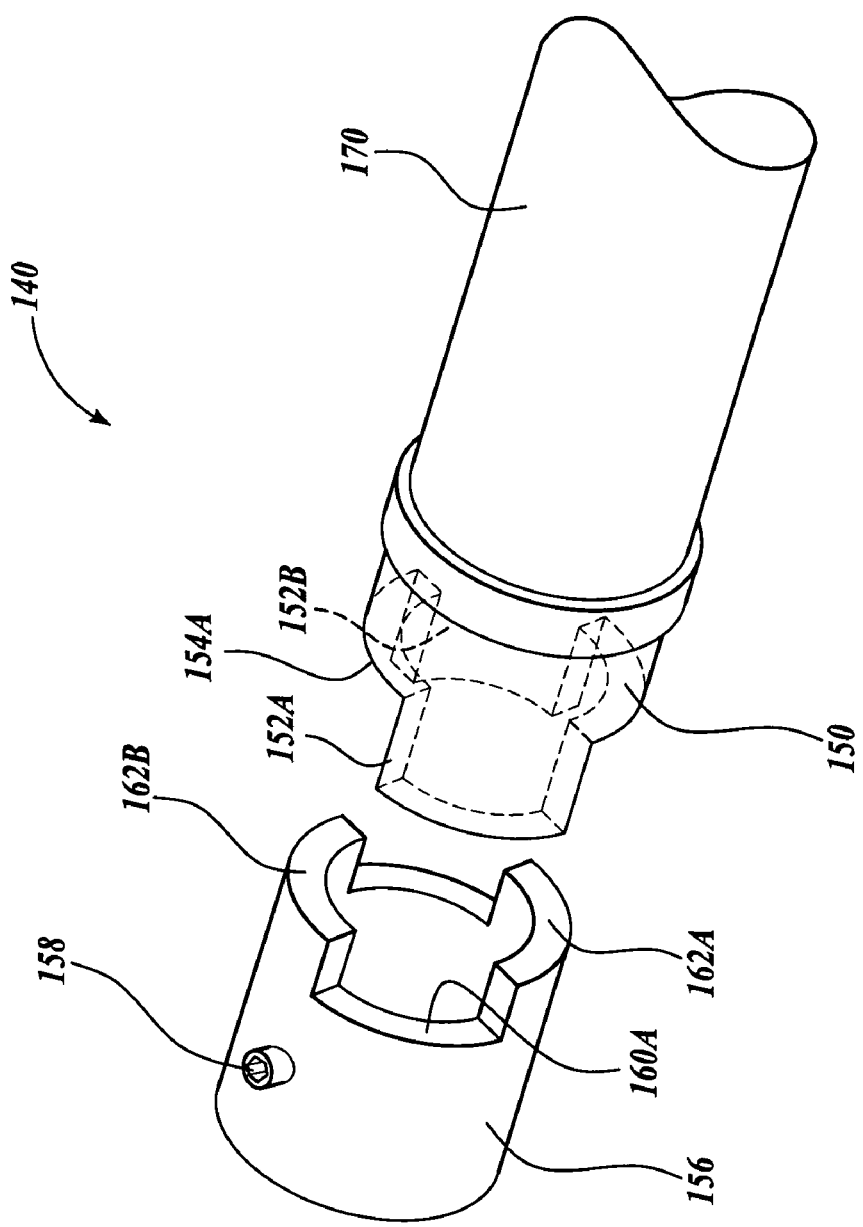
FIG. 6 shows a perspective view of the interface between the tangs and notches on interconnecting members of the shaft adapter shown in FIG. 5.

FIG. 6 illustrates the interlocking elements on the shaft adapter 150 and the rotary adapter 156 in the selectively rotatable shaft coupler 140. As shown, the first end of the shaft adapter 150 is adapted to be secured to the endoscope shaft 170 and the second end has two opposing tangs 152A,B alternating with two opposing notches 154A,B. The rotary adapter 156 has a corresponding set of tangs 162A,B and notches 160A,B which fit within the notches 154A,B and tangs 152A,B of the shaft adapter 150, respectively. As the rotary adapter 156 is rotated in the threaded collar 144, the rotary adapter and the shaft adapter separate or are faced closer together because the shaft adapter is held by the circular flange 182 in the annular slot. The length of the tangs and notches are chosen to allow continued slideable engagement through the desired range of endoscope shaft rotation.

Referring now to FIG. 5, in operation, the rotation of the endoscope shaft 170 causes the flange 180 on the shaft adapter 150 to rotate in the annular slot 182 in the collar 144. During rotation of the shaft adapter 150, the tangs on the shaft adapter engage in the notches of the rotary adapter, causing the rotary adapter 156 to rotate along with the endoscope shaft 170. As the rotary adapter 156 rotates in a first direction (e.g. clockwise), the engagement pin 158 moves along the grooves 146 of the threaded collar 144, causing the rotary adapter to move axially away from the shaft adapter until the engagement pin 158 contacts the stop pin 148A, thereby preventing further clockwise rotation. Similarly, when the rotation is in the counterclockwise direction, the rotary adapter moves toward the shaft adapter until the stop pin 148B prevents further rotation. Due to the circular flange 182 of the shaft adapter being retrained in the annular slot, the shaft adapter is not able to move axially in the channel during rotation of the shaft. Therefore, the effective length of the endoscope shaft does not change during rotation. This aspect of the invention advantageously allows the axial position of the endoscope tip to be maintained in the body during rotation. Furthermore, the components in the endoscope shaft do not contract or stretch during rotation.

Although the embodiment shown in FIG. 5 uses two stop pins 148A,B, it will be appreciated that a single stop pin 148B could be used by limiting the depth of the threads in the collar 144 such that the engagement pin 158 on the rotary adapter 156 cannot ride in the threaded grooves and thereby limiting rotation of the endoscope shaft 170.

Figure 7:
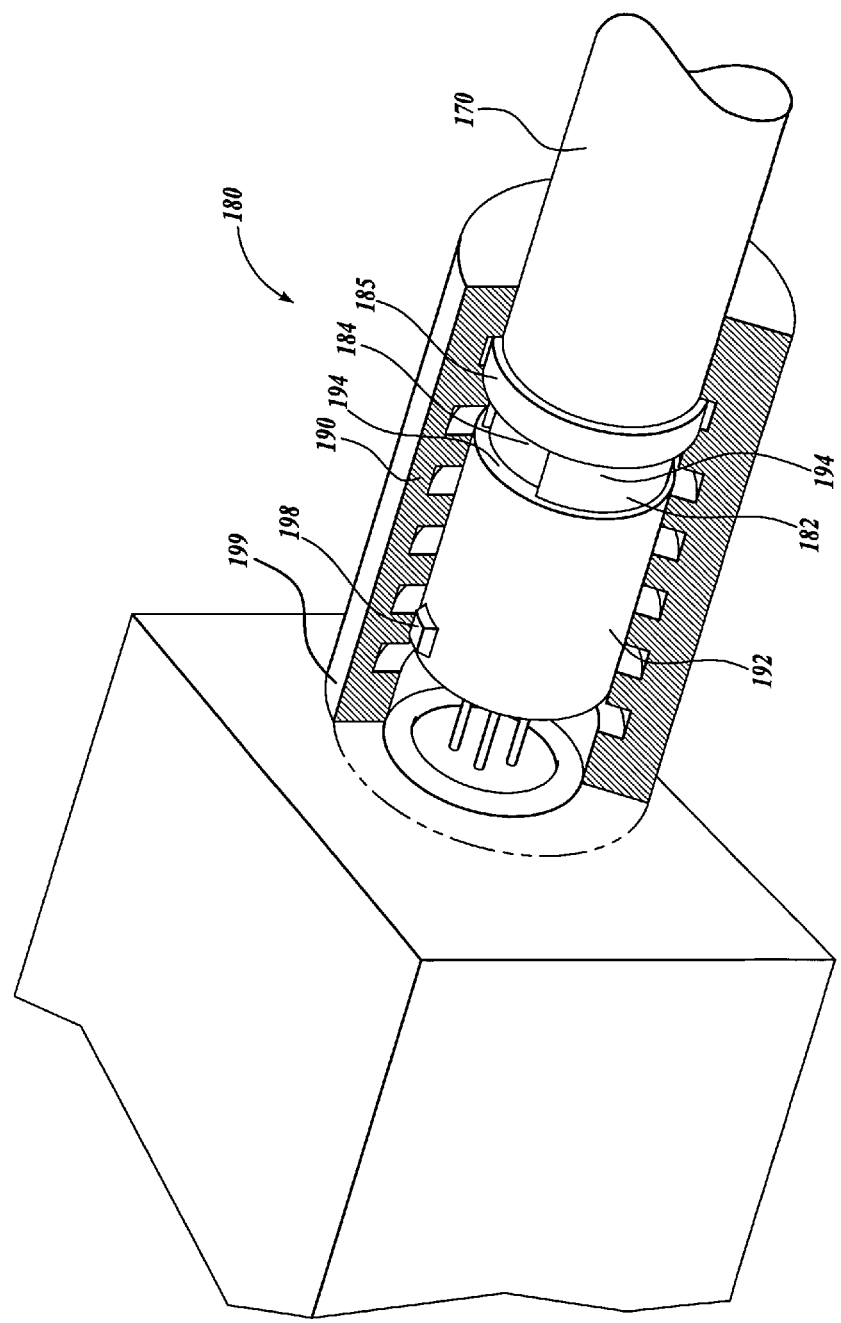
FIG. 7 illustrates yet another embodiment of a selectively rotatable shaft coupler that maintains the effective length of the endoscope shaft during rotation, in accordance with the present invention.
Figure 8A:
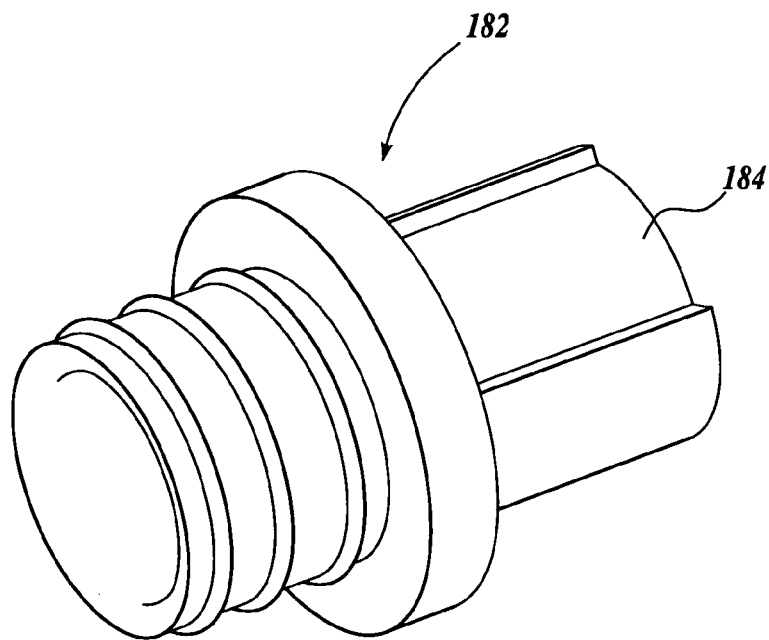
FIG. 8A shows a perspective view of a shaft adapter having grooves along the longitudinal axis in accordance with one embodiment of the present invention.
Figure 8B:
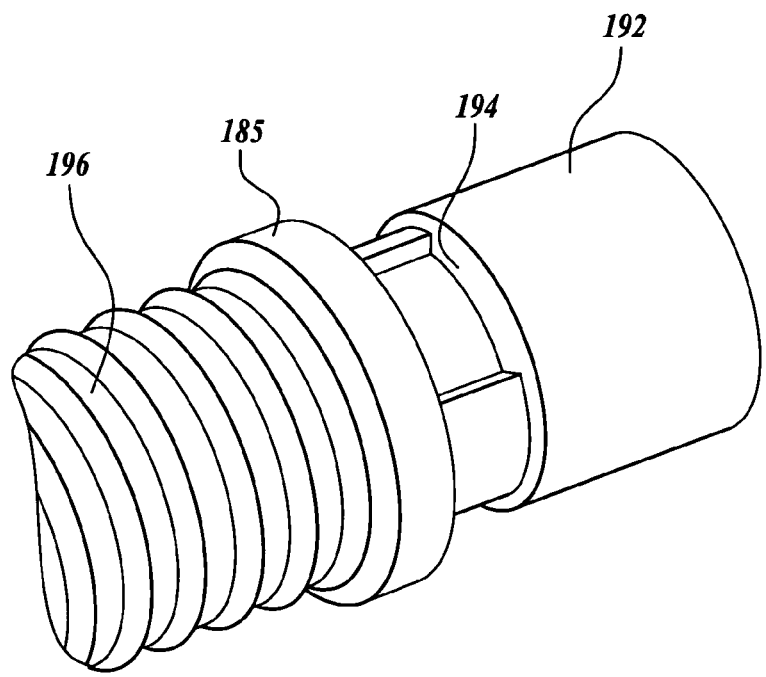
FIG. 8B shows a perspective view of the interface between the shaft adapter having grooves and a rotary adapter having corresponding ribs, in accordance with one embodiment of the present invention.

FIG. 7 is a partial cutaway drawing illustrating an alternative embodiment of a selectively rotatable shaft coupler 180 that attaches an endoscope shaft to a collar 190. The shaft coupler 180 maintains the effective length of the endoscope shaft during rotation. In the embodiment shown in FIG. 7, a shaft adapter 182 has a set of grooves 184 cut along its longitudinal axis that slidably engage a corresponding set of ribs 194 on a rotary adapter 192. An engagement pin 198 on the rotary adapter rides in the threaded grooves of the collar 190 and a stop 199 at the end thereof prevents further axial movement of the rotary adapter, thereby limiting rotation. The longitudinal grooves 184 on the shaft adapter 182 are best shown in FIG. 8A. FIG. 8B illustrates the rotary adapter 192 with ribs 194 slidably engaged in the grooves 184 on the shaft adapter 182. In the embodiment shown, the endoscope shaft 196 is corrugated to provide a secure attachment to the shaft adapter 182. A circular flange 185 allows the rotary adapter 182 to rotate in the collar (see FIG. 7), but prevents axial movement of the shaft adapter 182, thereby maintaining the effective length of the endoscope shaft during rotation. The rotatable shaft coupler 180 is preferably assembled by forming the collar 190 in two halves that are fitted over the rotary adapter 192 and the shaft adapter 182.

Figure 9:
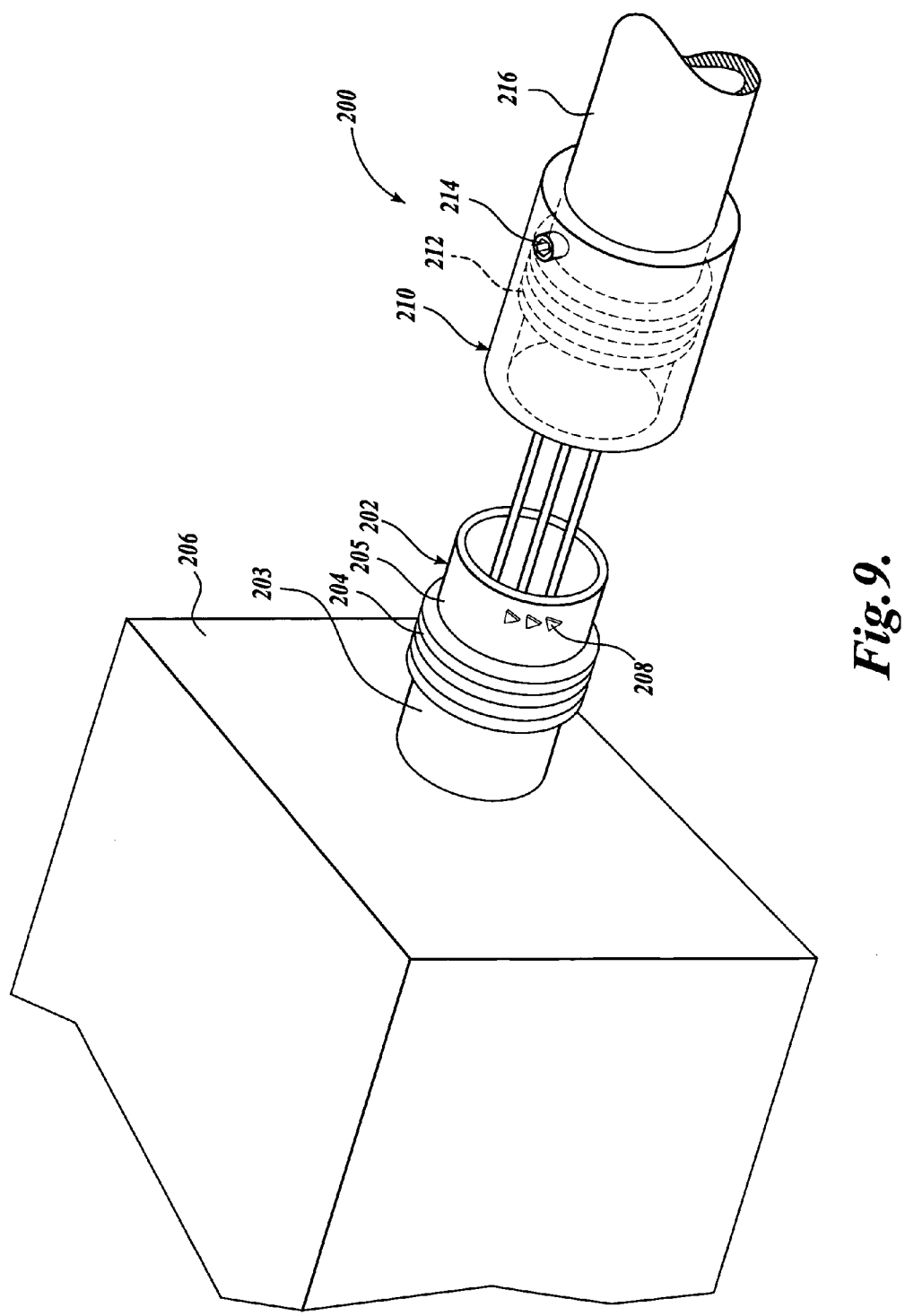
FIG. 9 shows a selectively rotatable shaft coupler having a non-rotatable shaft adapter in accordance with one embodiment of the present invention.

In another aspect, the present invention provides a selectively rotatable shaft coupler 200 having a shaft adapter with a first end non-rotatably fixed to a housing or other object and a second end adapted to rotatably receive an endoscope shaft. As shown in FIG. 9, the coupler 200 comprises a shaft adapter 202 with a first end 203 that is non-rotatably attached to a housing 206 and a second end 205 sized to rotatably receive an end of a shaft 216. The shaft adapter 202 has a threaded section 204 midway between the first end 203 and the second end 205. Positioned between the threaded section 204 and the second end 205 is a set of ratchets 208 capable of functioning as one-way stop elements as further described below. Also included in the coupler 200 is a collar 210 non-rotatably secured over an end of a shaft 216. The collar 210 has a stop pin extending inwardly toward the shaft 217 and located at a position chosen to stop rotation of the shaft 216. The shaft 216 has a threaded section 212 at or near its proximate end, the threaded section capable of screwing onto the threaded section 204 on the shaft adapter 202. In operation, the collar 212 is secured over the end of the shaft 216. The shaft 216 is then screwed onto the shaft adapter 202 over the ratchets 208 in a clockwise direction. Once the threaded section 212 of the shaft 216 is screwed onto the threaded section 204 of the shaft adapter 202, the shaft 216 can be rotated in a clockwise direction until the end of the shaft 216 and/or collar 210 contacts the wall of the housing 206. Rotation of the shaft 216 in a counterclockwise direction is permitted until the stop element 214 on the collar 210 contacts the ratchets 208, thereby preventing further counterclockwise rotation.

Figure 10A:
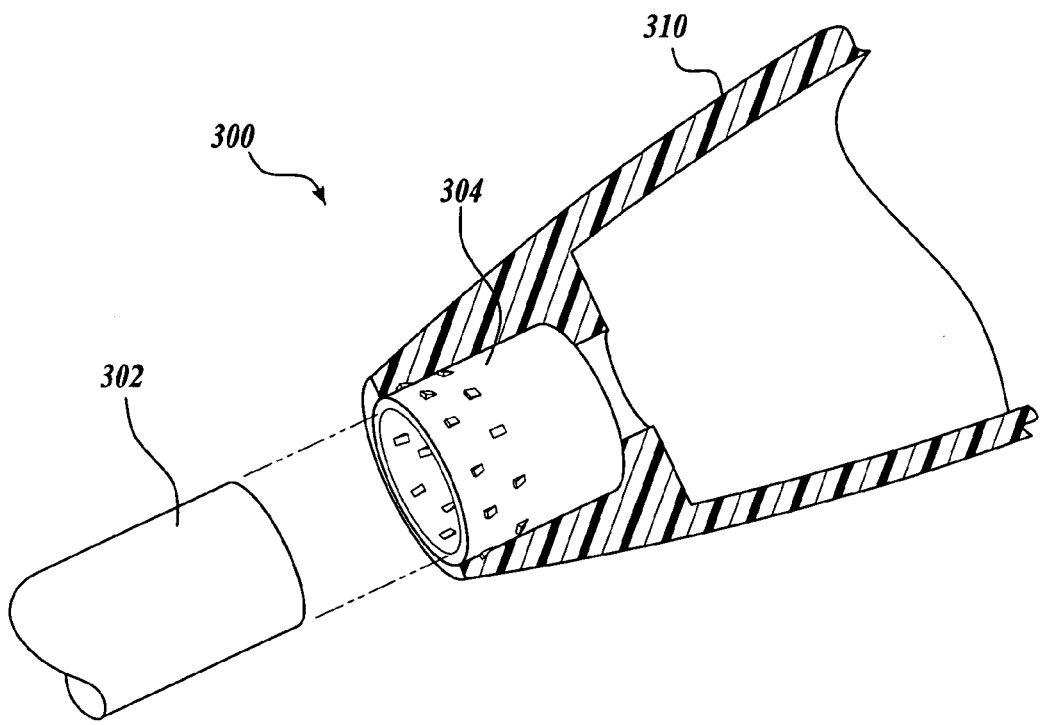
FIG. 10A illustrates a shaft retainer having inward and outward facing barbs, in accordance with another embodiment of the invention.
Figure 10B:
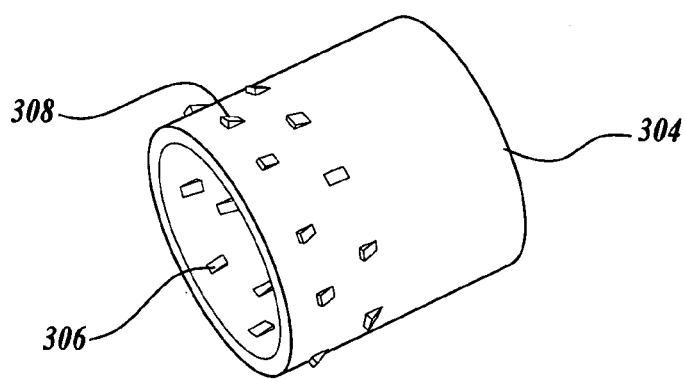
FIG. 10B shows a perspective view of the shaft retainer having inward and outward facing barbs in accordance with one embodiment of the invention.

In another aspect, the present invention provides a shaft coupling system for connecting a proximal end of an endoscope shaft 302 to a housing 310 or other structure without the use of adhesive or epoxies. A representative embodiment of the shaft coupling system 300 is shown in FIG. 10A. As shown, an endoscope shaft 302 is coupled to the housing 310 via a shaft retainer 304 that is press-fit into the housing 310. As shown more clearly in FIG. 10B, the shaft retainer 304 has a cylindrical hollow shape that is sized to fit into the housing 310. The outward surface of the shaft retainer 304 has a plurality of outward extending barbs 308 capable of securing the shaft retainer 304 into the housing 310. The inward surface of the shaft retainer body has a plurality of inward rearwardly extending barbs 306 that are capable of securing the endoscope shaft 302 into the shaft retainer. The shaft retainer 304 may additionally have a circular flange at one end to ease the insertion of the endoscope shaft 302.

The shaft retainer 304 may be made out of metal and be stamped to form the plurality of inward rearwardly and outwardly extending barbs. The stamped shaft retainer 304 may then be press-fit into the housing 310. In operation, the outwardly extending barbs 308 on the shaft retainer 304 secure the retainer ring in the housing without the need for adhesives or epoxies. Once the shaft retainer is secured in the housing, the endoscope shaft 302 is fitted into the housing via the inward rearwardly extending barbs 306 on the shaft retainer 304.

Figure 11A:
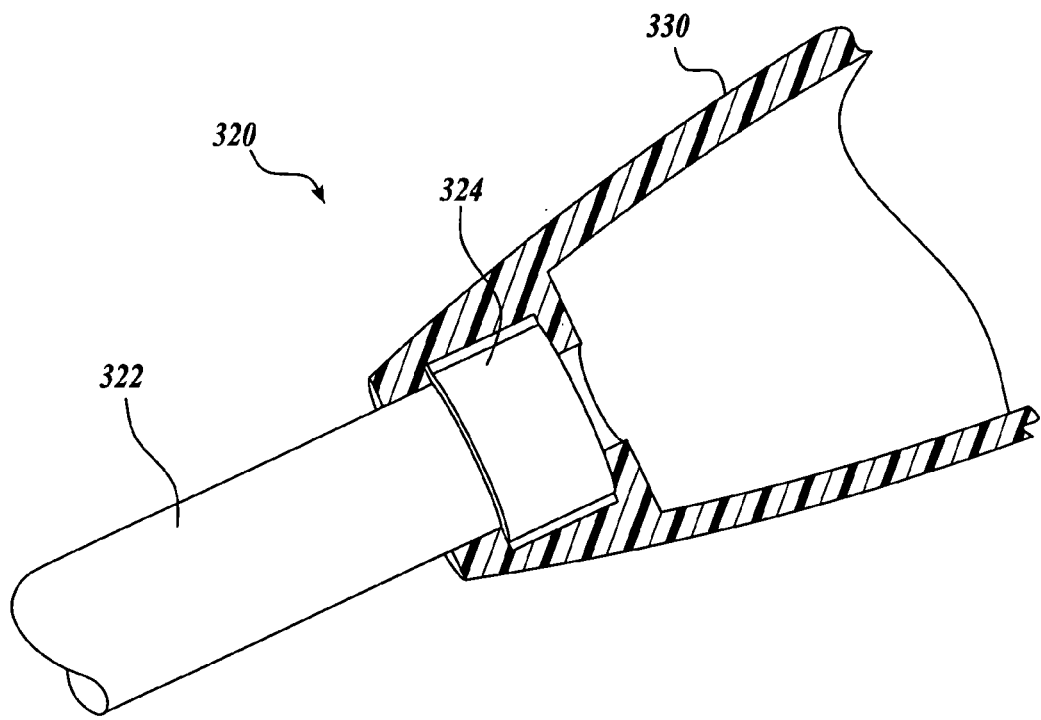
FIG. 11A illustrates an alternative embodiment of a shaft retainer having anti-rotation bosses coupled to a breakout box housing.
Figure 11B:
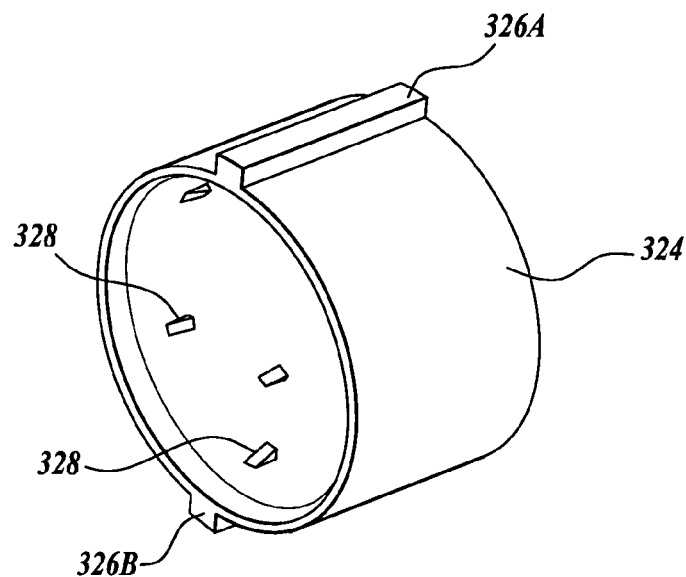
FIG. 11B shows a perspective view of the shaft retainer having anti-rotation bosses in accordance with one embodiment of the invention.

An alternative embodiment of a shaft coupling system 320 is shown in FIG. 11A. In this embodiment, an endoscope shaft 322 is secured in a shaft retainer 324 having one or more anti-rotation bosses. The shaft retainer 324 is fitted into a housing 330 having pockets or slots that are sized to receive the one or more anti-rotation bosses. As shown more clearly in FIG. 11B, the shaft retainer 324 has two anti-rotation bosses 326A, 326B that protrude from the outward facing side of the shaft retainer body. The inward facing side of the shaft retainer body comprises a plurality of inward rearwardly extending barbs 328 capable of securing the endoscope shaft 322. The shaft retainer with anti-rotation bosses 324 may be injection molded and fitted onto the proximal end of an endoscope shaft, wherein the inwardly extending barbs 328 secure the endoscope shaft without the need for adhesives or epoxies. The shaft retainer secured to the endoscope shaft may then be assembled with two halves of the housing, the one or more anti-rotation bosses fitted into preformed pockets in the housing. The coupling system 320 thereby allows for a secured connection between the endoscope shaft and a housing without allowing rotation or pull-out of the endoscope shaft and without the need for adhesives or epoxies.

While the preferred embodiment of the invention has been illustrated and described, it will be appreciated that various changes can be made therein without departing from the scope of the invention.

The embodiments of the invention in which an exclusive property or privilege is claimed are defined as follows:

1. A system for rotatably coupling a shaft of an insertable medical device to a housing while maintaining the effective length of the shaft during rotation, the system comprising: (i) a shaft adapter having a hollow body with a first end adapted to be secured to an end of a shaft of an insertable medical device, a second end adapted to be slidably connected to a rotary adapter, and a circular flange adjacent to the first end; (ii) a collar extending from the housing with a first end adapted to receive the flange on the shaft adapter and a threaded lumen with a first stop element and a second stop element, wherein the first stop element and the second stop element are spaced apart from one another at a predetermined width inside the collar; and (iii) a rotary adapter having a hollow body with a first end adapted to slidably connect to the second end of the shaft adapter and a second end comprising an engagement element, wherein the engagement element rides inside the threads of the collar, wherein rotation of the rotary adapter in the threaded collar causes incremental movement of the rotary adapter along the collar lumen until either the engagement element contacts the first stop element on the collar, limiting further rotation in the clockwise direction, or until the engagement element contacts the second stop element on the collar, limiting further rotation in the counterclockwise direction, wherein the effective length of the shaft is maintained during rotation.

2. The system of claim 1, wherein the shaft adapter and the rotary adapter are slidably connected with interfacing tangs and notches.

3. The system of claim 1, wherein the shaft adapter and the rotary adapter are slidably connected with interfacing grooves and ribs.

4. A system for rotatably coupling a shaft of an insertable medical device to a housing, the system comprising: (i) a shaft adapter having a rotatably securable hollow body with a first end adapted to be secured to an end of a shaft of an insertable medical device and a second end adapted to be rotatably attached to a collar; (ii) a collar extending from the housing that rotatably receives the shaft adapter; (iii) a circular flange located on the shaft adaptor capable of limiting the rotation of the shaft adapter with respect to the housing; and (iv) a bore within the collar and a cap secured over the bore such that the flange is movable in the bore by rotation of the shaft.

5. A system for rotatably coupling a shaft of an insertable medical device to a housing, the system comprising: (i) a shaft adapter having a rotatably securable hollow body with a first end adapted to be secured to an end of a shaft of an insertable medical device and a second end adapted to be rotatably attached to a collar; (ii) a collar extending from the housing that rotatably receives the shaft adapter, wherein at least a portion of the collar is threaded; (iii) at least two stop elements capable of limiting the rotation of the shaft adapter with respect to the housing, wherein the stop elements are located on the collar, wherein the space between the stop elements determines the range of shaft rotation; and (iv) an engagement element located on the shaft adapter body, wherein the engagement element rides in the grooves of the threaded collar, wherein rotation of the shaft adapter in the collar causes axial movement of the shaft adapter along the collar until the engagement element contacts the first or second stop element.

6. A system for rotatably coupling a shaft of an insertable medical device to a housing while maintaining the effective length of the shaft during rotation, the system comprising: an insertable medical device shaft having a proximal end and a distal end and one or more lumens therein; a housing; a threaded collar attached to the housing; a shaft adapter for rotatably coupling the shaft to the housing, the shaft adaptor sized to rotate in the threaded collar, the shaft adapter having a first end adapted to be secured to the proximal end of the shaft, a second end adapted to slidably connect to a rotary adapter and means to prevent the axial motion of the shaft;

and a rotary adapter for selectively rotating the shaft with respect to the housing, wherein the rotary adaptor is intermediate the shaft adapter and the housing having a hollow body with a first end adapted to slidably connect to the second end of the shaft adapter, wherein the shaft adapter and the rotary adapter cooperate to limit rotation of the shaft, wherein the effective length of the shaft is maintained during rotation.

7. The system of claim 6, wherein the rotary adapter comprises an engagement element adapted to engage the threads of the collar.

8. The system of claim 7, wherein the threaded collar has at least one stop element.

* * * * *